US010299779B2

(12) United States Patent
Shepherd et al.

(10) Patent No.: US 10,299,779 B2
(45) Date of Patent: May 28, 2019

(54) SOFT BLADDER FOR INTERABDOMINAL SURGERY

(71) Applicant: President and Fellows of Harvard College, Cambridge, MA (US)

(72) Inventors: Robert F. Shepherd, Brooktondale, NY (US); George M. Whitesides, Newton, MA (US); Bobak Mosadegh, New York, NY (US)

(73) Assignee: President and Fellows of Harvard College, Cambridge, MA (US)

( * ) Notice: Subject to any disclaimer, the term of this patent is extended or adjusted under 35 U.S.C. 154(b) by 414 days.

(21) Appl. No.: 14/518,433

(22) Filed: Oct. 20, 2014

(65) Prior Publication Data
US 2015/0112130 A1    Apr. 23, 2015

Related U.S. Application Data

(60) Provisional application No. 61/892,595, filed on Oct. 18, 2013.

(51) Int. Cl.
*A61B 1/00* (2006.01)
*A61B 17/02* (2006.01)
(Continued)

(52) U.S. Cl.
CPC ........ *A61B 17/0218* (2013.01); *A61B 1/3132* (2013.01); *A61B 1/32* (2013.01); *A61B 1/00082* (2013.01); *A61B 2017/00557* (2013.01); *A61B 2017/00831* (2013.01); *A61B 2017/0225* (2013.01)

(58) Field of Classification Search
CPC ..... A61B 17/0218; A61B 1/32; A61B 1/3132; A61B 1/04; A61B 2107/0225; A61B 2107/00557; A61B 2107/00831; A61B 1/00082
See application file for complete search history.

(56) References Cited

U.S. PATENT DOCUMENTS 3,343,864 A * 9/1967 Baer ................... B25J 15/0009
294/119.3
3,730,186 A * 5/1973 Edmunds, Jr. ....... A61B 17/122
128/DIG. 25

(Continued)

FOREIGN PATENT DOCUMENTS

WO    WO-2012/148472 A2    11/2012

OTHER PUBLICATIONS

International Search Report and Written Opinion issued by the U. S. Patent and Trademark Office as International Searching Authority for Application No. PCT/US14/61387 dated Jun. 25, 2015 (10 pages).

*Primary Examiner* — Timothy J Neal
(74) *Attorney, Agent, or Firm* — Wilmer Cutler Pickering Hale and Dorr LLP

(57) ABSTRACT

A surgical device for displacement of organs within a body cavity for providing at least visual access to a selected site includes an expandable bladder, wherein the elasticity of the bladder varies across the surface of the bladder, said variation in elasticity selected to provide a predetermined, non-spherical shape when expanded; and a valve on the proximal end on the inflatable bladder for introduction of a pressurizing gas into the soft bladder.

9 Claims, 6 Drawing Sheets

(51) Int. Cl.
*A61B 1/32* (2006.01)
*A61B 1/313* (2006.01)
*A61B 17/00* (2006.01)

(56) References Cited

U.S. PATENT DOCUMENTS

| | | | | |
|---|---|---|---|---|
| 5,308,327 | A | * | 5/1994 | Heaven ............ A61B 17/00234 604/103.09 |
| 5,776,159 | A | * | 7/1998 | Young ................ A61B 17/0218 128/898 |
| 5,779,728 | A | | 7/1998 | Lunsford et al. |
| 7,331,273 | B2 | * | 2/2008 | Kerekes ................ B62D 35/005 92/92 |
| 7,744,617 | B2 | * | 6/2010 | Lunsford ........... A61B 1/00082 600/184 |
| 2003/0004493 | A1 | * | 1/2003 | Casey ................. A61M 25/005 604/525 |
| 2007/0032788 | A1 | * | 2/2007 | Edwards ............ A61B 18/1206 606/41 |
| 2011/0112373 | A1 | * | 5/2011 | Ainsworth ......... A61B 17/0218 600/207 |
| 2014/0364892 | A1 | | 12/2014 | Okoniewski et al. |

\* cited by examiner

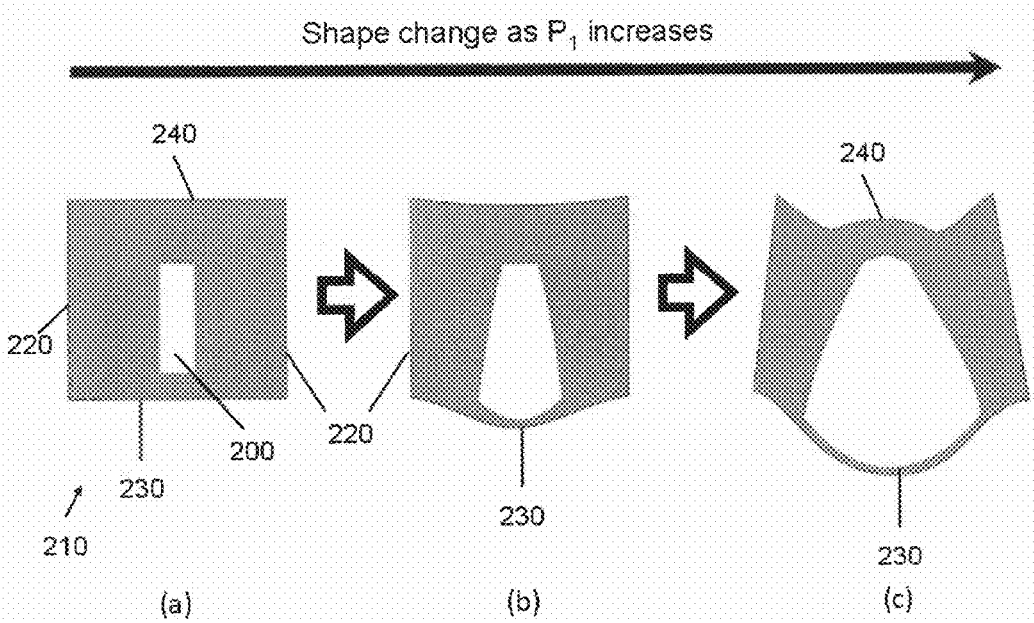

SOFT BLADDER FOR INTERABDOMINAL SURGERY

RELATED APPLICATIONS

The application claims the benefit of priority under 35 U.S.C. § 119(e) to U.S. Provisional Application Ser. No. 61/892,595, filed Oct. 18, 2013, the contents of which are incorporated by reference.

GOVERNMENT FUNDING CLAUSE

The present invention was made with United States government support under Grant Nos. W911NF-11-1-0094 and awarded by Defense Advanced Research Projects Agency (DARPA). The United States government has certain rights in this invention.

INCORPORATION BY REFERENCE

All patents, patent applications and publications cited herein are hereby incorporated by reference in their entirety in order to more fully describe the state of the art as known to those skilled therein as of the date of the invention described herein.

BACKGROUND

Laparoscopic surgery is a surgical technique in which operations in the abdomen are performed through small incisions (usually 0.5-1.5 cm). There are a number of advantages to the patient with laparoscopic surgery versus an open surgical procedure. These include reduced pain due to smaller incisions and hemorrhaging, and shorter recovery time.

Laparoscopic surgery is accomplished using a laparoscope. There are two types: (1) a telescopic rod lens system, that is usually connected to a video camera (single chip or three chip), or (2) a digital laparoscope where the charge-coupled device is placed at the end of the laparoscope, eliminating the rod lens system. Also attached is a fiber optic cable system connected to a 'cold' light source (halogen or xenon), to illuminate the operative field, inserted through a cannula or trocar to view the operative field. The abdomen is usually insufflated, or essentially blown up like a balloon, with carbon dioxide gas. This elevates the abdominal wall above the internal organs like a dome to create a working and viewing space. The camera on a movable stick can be inserted into the abdominal cavity, but has limited degree of motion and line of sight.

A fundamental problem in general laparoscopic surgery is that surgeons do not easily have line-of-sight access to internal organs. Inflating the abdominal cavity with $CO_2$ does not provide line-of-sight access, as organs may still be in the way. Various approaches currently exist to make it easier for surgeons to get access to fields of interest for a surgical procedure, but each has limitations.

In addition, $CO_2$ embolism, although rare, is potentially a fatal risk of laparoscopic surgery. $CO_2$ embolisms occur by the inadvertent insertion of the Veress needle into the blood vessels either on the abdominal wall, peritoneal, or open vessels on organs (e.g., liver surface during gall bladder dissection).

Equipment and methods for improving laparoscopic surgery are desired.

SUMMARY

This invention provides a soft bladder for use in interabdominal surgery. The soft bladder is introduced into the abdominal cavity in a deflated state and can be inflated inside the patient. The materials, shape and composition of the soft bladder is selected to provide a predetermined expanded configuration to the soft bladder. Embedded patterns program the bladder to inflate in a predefined manner, providing line of sight access to specific parts of the abdominal cavity.

In one or more embodiments, the soft bladder is self-sealing. The surgeon can insert surgical instruments through the self-sealing bladder and gain easy access to specific organs. In other embodiments, the bladder inflates to provide a cavity within the abdomen, thereby providing a clear line of sight within the abdomen. Surgical instruments can be introduced, e.g., from the same or a separate incision point, into the cavity provided by the inflatable bladder. The bladder can also be used to displace, rotate, or stabilize organs. Since the bladder is enclosed and self-sealing, the risk of $CO_2$ embolism is reduced.

In one aspect, a surgical device for displacement of organs within a body cavity for providing visual access to a selected site includes an expandable non-permeable bladder, wherein the elasticity of the bladder varies across the surface of the bladder, the variation in elasticity selected to provide a predetermined, non-spherical shape when expanded so as to provide visual access to a target body site.

In one aspect, a surgical device for displacement of organs within a body cavity for providing at least visual access to a selected site includes an expandable bladder, wherein the elasticity of the bladder varies across the surface of the bladder, said variation in elasticity selected to provide a predetermined, non-spherical shape when expanded; and a valve in flow communication with the inflatable bladder for introduction of a pressurizing gas into the soft bladder.

In one or more embodiments, the surgical device further includes an insertion housing for housing the expandable non-permeable bladder in an unexpanded state.

In any of the preceding embodiments, the elasticity of the expandable bladder is selected of provide non-uniform bladder expansion, and for example, the expandable bladder is comprised of walls of different thickness, said different in wall thickness selected to provide the variation in elasticity across the surface of the bladder, or a portion of the expandable bladder comprises reinforcement, said reinforcement selected to provide the variation in elasticity across the surface of the bladder, and by way of example, the reinforcement is selected from fibers and tape.

In any of the preceding embodiments, the surgical device further includes at least one port in the expandable non-permeable bladder adapted to allow a surgical instrument to pass therethrough.

In any of the preceding embodiments, the surgical device further includes a laparoscopic tool having a flexible tube with a camera at its distal end.

In any of the preceding embodiments, the expandable non-permeable bladder is self-sealing to punctures.

In any of the preceding embodiments, the uninflated soft bladder is ovoid in shape, or the uninflated soft bladder is L-shaped, and for example, the shape and elasticity profile of the soft bladder is selected to provide an L7 shape on expansion.

In any of the preceding embodiments, the valve is a one-way valve, or a two-way valve.

In another aspect, a method of viewing organs within a body cavity includes introducing an expandable non-permeable bladder wherein the elasticity of the bladder varies across the surface of the bladder through a first incision into an abdominal cavity of a patient, and inflating the non-permeable bladder wherein the variation in elasticity across the bladder surface causes the bladder to expand non-uniformly into a predetermined shape, wherein the expanded bladder extends the abdominal wall and displaces internal organisms to provide visual access to a target site.

In one or more embodiments, the method further includes inserting surgical equipment into the expandable non-permeable bladder, such as for example, a camera.

In any of the preceding embodiments, a second incision is made to introduce other bladders that can be inflated to provide additional maneuverability to organs.

In any of the preceding embodiments, a further incision is made to introduce surgical equipment accessible to the target site.

BRIEF DESCRIPTION OF THE DRAWINGS

The invention is described with reference to the following figures, which are presented for the purpose of illustration only and are not intended to be limiting.

FIGS. 3(a)-3(c) illustrate the principle of directed expansion and deformation and a bladder in (a) a resting state, in which the pressure inside the bladder ("$P_1$") is equal to the pressure outside the bladder, such as the atmospheric pressure ("$P_{ath}$"); (b) a pressurized state, in which the pressure inside the bladder is greater than the pressure outside the chamber; and (c) in a deformed state, in which the pressure inside the bladder is greater than a predetermined threshold ("$P_{ath}$"), according to one or more embodiments.

DETAILED DESCRIPTION

Figure 1:
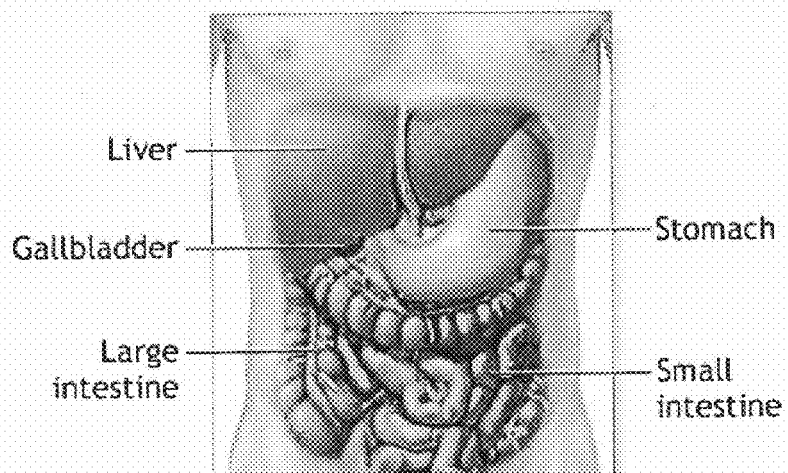
FIG. 1 is an illustration of the human abdominal cavity with the abdominal wall removed to show the body interior.

FIG. 1 illustrates the human abdominal cavity and shows the many organs in abutting and overlapping proximity with one another. It is important for surgeons to be able to obtain a clear view of the organs being operated on during laparoscopic surgery, which is difficult in the close confines of the abdominal cavity. As noted, conventional procedures use a gas, such as $CO_2$, to inflate the abdomen. While this provides additional space, it does not serve to move or displace organs that may nonetheless interfere with surgery. Thus, by way of example, if it were desired to perform a surgical procedure on the liver, the surgeon would need to carefully navigate around the stomach, gall bladder and large intestine, for example.

In one or more embodiments, an inflatable bladder is provided that is capable of inflation into a predetermined shape selected to fit into the abdominal cavity and to displace selected organs to provide physical and visual access to an organ of interest. The bladder is introduced into the abdomen in a deflated state and is inflated to a desired size and shape in situ. Upon expansion, the inflatable bladder moves organs out of the way and permits visual and/or physical access to an organ of interest during surgery. In one or more embodiments, the bladder is made of a self-sealable material that allows surgical tools to penetrate the bladder, without leaking the inflation gas (typically $CO_2$).

Figure 2A:
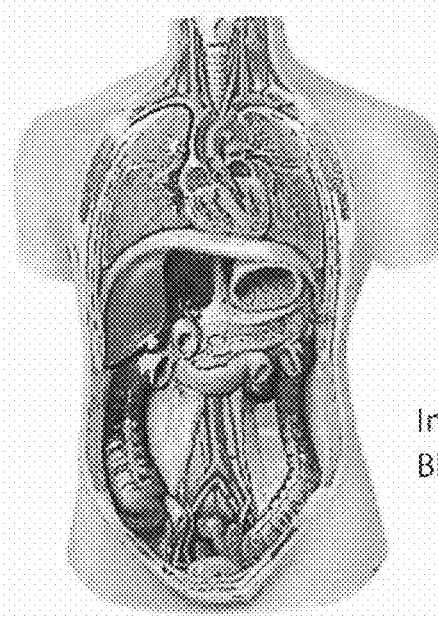
FIG. 2A is an illustration of the human body cavity highlighting the location of the liver and identifying organs potentially interfering in liver surgery.
Figure 2B:
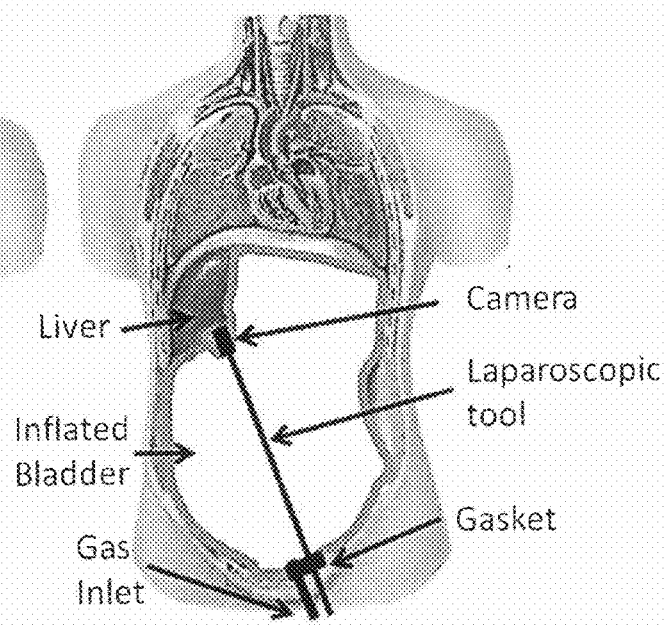
FIG. 2B is an illustration of an inflatable bladder located within the abdominal cavity to displace organs and permit a free line of sight.

FIG. 2 illustrates the basic principles of the device. FIG. 2A is a different view of the abdominal cavity, with certain organs removed to show the location of the liver. FIG. 2B illustrates the location of an expanded soft bladder in the abdominal cavity. The shaped soft bladder can simultaneously separate the internal organs from the abdominal wall and provide an internal working environment for a surgeon. In one or more embodiments, the soft bladder is designed to expand so as to provide an unhindered visual view of a selected organ in the abdominal cavity, e.g., the liver, or elsewhere in the body. In one or more embodiments, the bladder does not expand uniformly in all directions. The bladder is designed to expand to a greater extent in selected areas, the areas being selected in accordance with a predetermined three dimensional geometry. As discussed in detail below, an inflatable bladder is introduced into the abdominal cavity in a deflated state and is inflated in situ to a shape selected to push other organs out of the way, while providing access in this current embodiment to the liver. See FIG. 2B.

In one or more embodiments, the bladder is made from a physiologically compatible elastomeric material that is highly extensible or expandable. The balloon is preferably non-permeable and specifically non-gas permeable. In preferred embodiments, the elastomer is an FDA-approved material or a material that is approved by a governmental regulatory agency for use in the human body. Materials currently used in other surgical procedures, such as polyvinyl chloride, polyethylene terephthalate, and nylon do not have the needed extensibility, therefore elastomers such as silicones and polyurethanes, may be used. In one or more embodiments, the elastomeric materials is a highly extensible material and is capable of expansion many fold expansion, e.g., 10×, 20× or higher.

In one or more embodiments, the bladder is prepared from elastomeric materials that are self-sealing. In particular, the balloon materials are capable of self-healing when punctured. The self-sealing property of the bladder permits instruments to pass through the bladder wall without deflation, loss of internal pressure or gas leak. The bladder can be prepared from polymers known to be capable of self-sealing. Exemplary polymers include silicone rubbers and polyurethanes. In other embodiments, bladders can be fiber reinforced to prevent crack formation around the puncture point that might otherwise lead to gas leakage. In other embodiments, the soft balloon can include reinforcing areas that provide mechanical strength to the balloon. Such reinforces, or struts, can be made by adding layers of thickness to the balloon in predetermined areas, such as through the balloon molding process or in a post molding application of reinforcing strips or tape.

In one or more embodiments, the soft bladder is made of one or more layers to provide different elastic moduli across different areas of the bladder surface. The differences in moduli cause the soft bladder to expand to different extents and degrees over the surface of the bladder, and thereby take on an expanded 3D shape that is determined, in part, by the restriction to expansion imposed by the higher elastic modulus. The variation in resistance to expansion allows the bladder to take on complex shapes upon expansion. The expanded bladder can have a "T" or "L" shape, or any other complex shape.

In one or more embodiments, the expandable bladder can have an "egg" shape—such that the tip of the expanding balloon can more easily deflect organs (as a wedge). The long axis length of the egg-shaped bladder can be selected to reach the specific organ. The length of the expanded bladder can be a factor of its initial size, the elasticity of the bladder material and the extent of inflation. In instances where it is desirable to rotate an organ, the uninflated bladder can have an "L" shape and then expand into an "L7" shape. The 7 can be altered to affect the degree of twist. As used herein, the "L7" term refers to expansion of a "L" shaped bladder into a "square" shaped bladder. In the initial "L" shape, the bladder can be wedged against the organ. Upon inflation, the organ is rotated as the walls of the bladder push against the organ in a differential manner (since the bladder inflates with greater displacement on one end than the other).

The elastic modulus can be varied in any acceptable manner. For example, the elastic modulus can be altered by varying the wall thicknesses of the bladder. In other embodiments, the elastic modulus can be increased by local incorporation of a reinforcing material that increases the modulus in the reinforced area. Strips of higher modulus material, such as tape or other adhesive polymer, can be used to provide the desired deformation. In other embodiments, threads or fibers, e.g., aligned threads or fibers, can be used to provide locally higher resistance to expansion and deformation.

The principle of local variation and selective deformation is illustrated in FIG. 3, in which a bladder is defined by an interior chamber 200 made from a soft rubber (elastomeric) 210 having a thicker, yet still pliable regions 240 and a thinner region 230. In certain embodiments, a high elastic modulus or thicker wall can be incorporated into the expandable bladder and used for sections where inflation is undesirable, while a low elastic modulus or thinner wall is used for regions of the bladder where extensibility is needed. Upon pressurization of the bladder, the soft-elastomer bladder expands (FIG. 3(*b*)). The soft-rubber's expansion is accommodated by bending (FIG. 3(*c*)). As the pneumatic actuator system is subjected to increasing pressure, the soft bladder takes on different and more complex shapes.

As used herein, "stiffness" refers to the resistance of the elastic body to deformation (e.g., extension) by an applied force. In general, elastic modulus is related to, but not the same as, stiffness. Elastic modulus is a property of the constituent material; stiffness is a property of a structure. That is, the elastic modulus is an intensive property of the material; stiffness, on the other hand, is an extensive property of the network and is dependent on the material modulus and the shape and boundary conditions. Because stiffness is a function of the Young's modulus, the material modulus can be used as a comparative measure of the relative stiffness of the channels walls and a predictor of deflection upon pressurization of the channel networks.

In certain embodiments, the soft bladder can be prepared using a mold configured to define a cavity having a desired geometry. For example, the mold can be configured to form a tube-like cavity in the molded device. The mold can be configured to define a cavity whose perpendicular cross-section is an arbitrary shape. The arbitrary shape can include a triangle, an equilateral triangle, a square, a rectangle, a pentagon, a hexagon, and a circle. The mold can define walls of different thickness so as to vary the elasticity (or stiffness) of the bladder over its surface. The mold can also accommodate additional materials, such as fiber or other reinforcing materials that permit the final soft bladder to vary the elasticity (or stiffness) of the bladder over its surface. In other embodiments, the mold can define individual sections that can be cast using different materials having different stiffness and/or elasticity.

In certain embodiments, the soft bladder can be pleated as illustrated in FIG. 6. The corners of the pleated structures can be designed to have soft, rounded edges to avoid harm to internal organs. In addition, fibers can be integrated into the bladder walls, which can aid in resealability. The outer surface of the material can be only elastomer and therefore soft to the touch. This approach would allow for thinner walls to be resealable. The pure elastomers are able to reseal but typically do so with thicker walls.

The abdominal bladder is designed to expand for specific applications and each bladder can be uniquely designed for expansion to a selected 3D shape based upon the surgical procedure of the size and gender of the patient. Thus, for example, the abdominal bladder can be designed to provide access to the liver, gall bladder, spleen, stomach, specific regions of the small or large intestine. The bladder can also be sized to accommodate patients of different sizes, e.g., from a child to a large adult.

In one or more embodiments, the expandable, soft surgical device is made of a single soft bladder, modified as described herein to provide the desired shape on expansion. In other embodiments, the device can be made of a plurality of interconnected bladders, each of which is modified as described herein to provide the desired shape on expansion.

A method of application of a soft bladder for interabdominal surgery according to one or more embodiments is now described. In a first step, the abdomen is inflated as in conventional laparoscopic processes to enlarge the abdominal cavity and raise the abdominal wall from the organs. The soft bladder can be introduced into the body using a protective housing. The protective housing can be a tubular body having a proximal end corresponding to the proximal end of the bladder (with the gas inlet), and a distal end corresponding to the distal end of the soft bladder. The protective housing may be made of any relatively hard, biologically non-reactive material including but not limited to plastic materials. A small insertion is made, again using conventional laparoscopic procedures, of a dimension common to the particular procedure and sufficient to accommodate the tools and instrumentation needed for the procedure. Other incisions may be made to accommodate additional surgical devices. To introduce the soft bladder into the patient, an incision, e.g., ranging from 5-10 mm, is made in the patient. Then, using standard laparoscopic techniques, a trocar and a trocar sleeve are inserted into the abdomen. After the trocar is removed, the trocar sleeve remains extending from the outside of the patient. The trocar sleeve preferably includes a one-way valve such that when the protective housing including the soft bladder is passed through the trocar sleeve into the abdomen of the patient, gas from inside the abdomen is not released. Next, a soft bladder (in the housing) is introduced into the abdominal cavity through the trocar sleeve in a deflated state. After the soft bladder is delivered through the trocar sleeve into the abdomen, the housing is then withdrawn. The soft bladder may be held in place in the abdomen by being held by a laparoscopic grasper that has been introduced into the abdomen from a separate incision. It will be appreciated that other methods and apparatuses may be used to insert the soft bladder into the abdomen of a patient.

In certain embodiments, the surgical instrumentation is housed within the balloon and is introduced into the abdominal cavity together with the soft bladder that also contains a camera at the tip of the instrument. The neck of the balloon forms a gas-tight sealing contact with the tools, e.g., by using a gasket. Once inserted, the soft bladder is inflated using pressurizing gas, e.g., $CO_2$ or other inert or physiologically benign gas (i.e. $N_2O$) via a separate inlet in the gasket. The balloon can be inflated using a hand pump or other methods conventionally used in laparoscopic interventions.

The soft bladder may also have additional openings or ports to allow for insertion of surgical instruments. These ports may be placed at desired locations on the surface of the bladder to allow for the insertion of appropriate surgical instruments at desired locations. Preferably, each of these ports includes a one-way valve to prevent gas inside the bag from escaping when an instrument is inserted there through.

The soft bladder is provided as a separate part from the laparoscopic tool or as a single integrated tool. In the case that it is a separate part, the bladder can be affixed to the laparoscopic tool by means of a mechanical connection (e.g., screw, clip, pneumatically activated fixture, magnetic seal). The pneumatic line that inflates the bladder can be separate from the laparoscopic tool, and therefore directly connected by a tubing to a pneumatic source. Alternatively, the pneumatic source can connect to the bladder via the mechanical connection used to attach the bladder to the laparoscopic tool. In the case the bladder is provided as a single unit with the laparoscopic tool, the pneumatic source can be connected to the bladder via the laparoscopic tool. Valves are used to regulate pressure within the bladder. The valves can be integrated either within the laparoscopic tool or housed externally from the laparoscopic tool.

Figure 4:
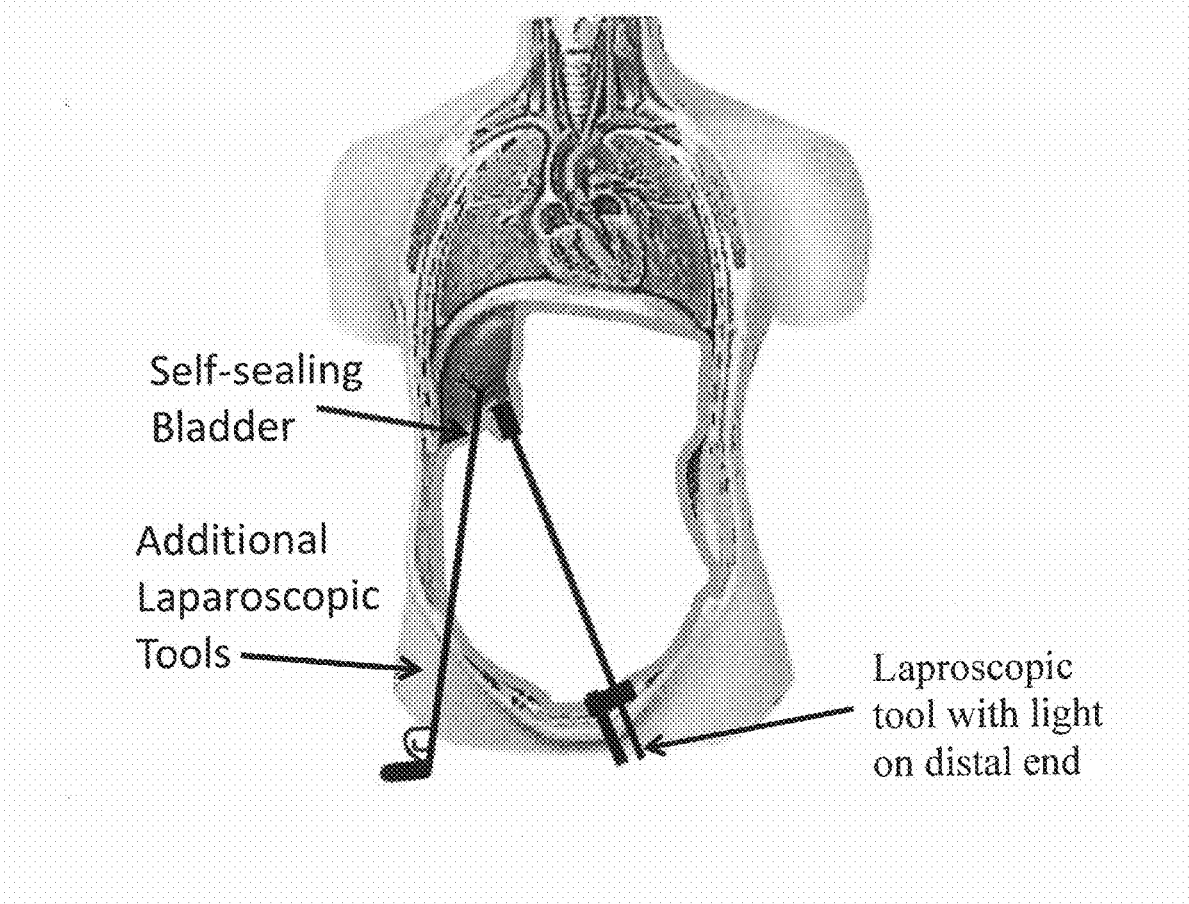
FIG. 4 is an illustration setting out the method of application of a soft bladder for interabdominal surgery and illustrating the locations of the self-sealing bladder and additional laparoscopic tool that can be inserted through the self-sealing bladder according to one or more embodiments.

FIG. 4 is an illustration setting out a method of application of a soft bladder for interabdominal surgery according to one or more embodiments. In a first step, the abdomen is inflated as in conventional laparoscopic processes to enlarge the abdominal cavity and raise the abdominal wall from the organs. A small insertion is made, again using conventional laparoscopic procedures, of a dimension common to the particular procedure and sufficient to accommodate the soft bladder in its deflated state. A second incision is made, again using conventional laparoscopic procedures, of a dimension common to the particular procedure and sufficient to accommodate the tools and instrumentation needed for the procedure. Next a soft bladder in a deflated state is introduced into the abdominal cavity through the first incision. The neck of the balloon forms a gas-tight sealing contact (using a gasket) with a connector to the gas source. Once inserted, the soft bladder is inflated using pressurizing gas, e.g., $CO_2$ or other inert or physiologically benign gas (i.e., $N_2O$) via a separate inlet in the gasket. The bladder is selected so that it in its enlarged and inflated state it displaces internal organs that may be obstructing view and access to the organ to be operated on. The surgical instrumentation is introduced into the abdominal through the second incision. The location of the second incision is selected to provide an unhindered access to the organ of interest, once the soft bladder has been inflated to move obstructing organs aside. The material properties of the bladder allow the instrument to puncture a hole without leakage of the pressurized gas inside the bladder.

Figure 5:
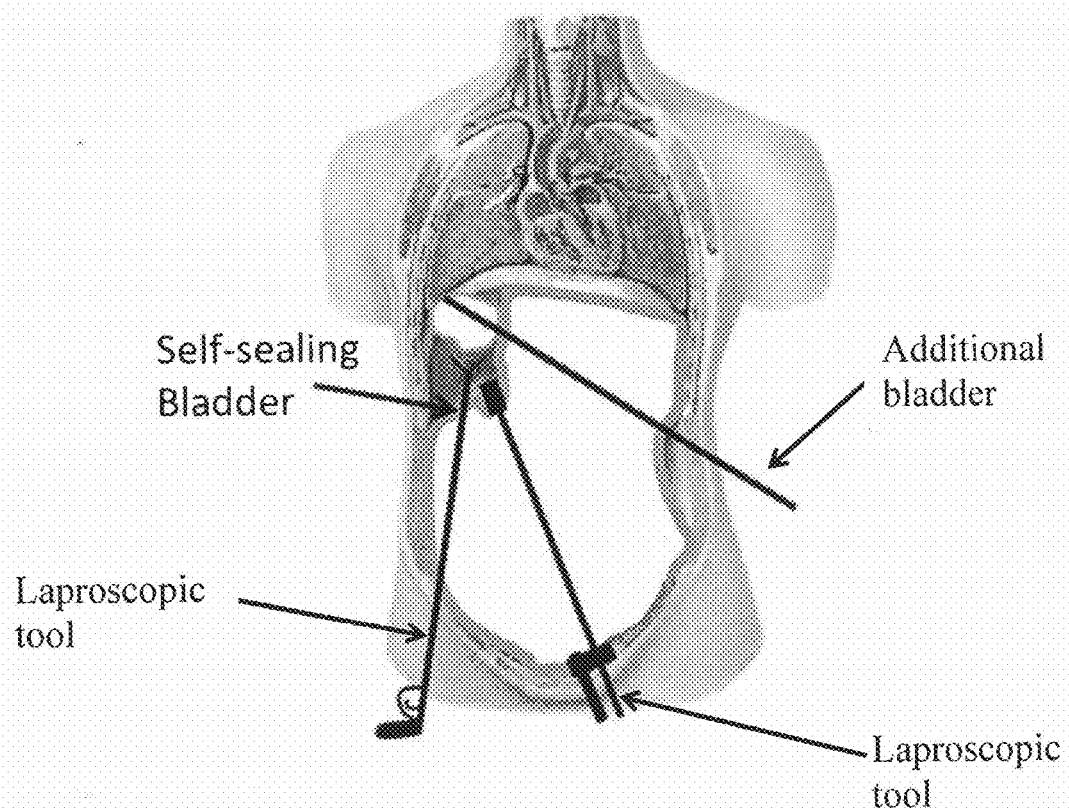
FIG. 5 is an illustration setting out the method of application of a soft bladder for interabdominal surgery and illustrating an additional bladder inserted through the self-sealing bladder to provide additional maneuverability according to one or more embodiments.

FIG. 5 is an illustration setting out a method of application of a soft bladder for interabdominal surgery according to one or more embodiments. In a first step, the abdomen is inflated as in conventional laparoscopic processes to enlarge the abdominal cavity and raise the abdominal wall from the organs. A small insertion is made, again using conventional laparoscopic procedures, of a dimension common to the particular procedure and sufficient to accommodate the soft bladder in its deflated state. A second incision is made, again using conventional laparoscopic procedures, of a dimension common to the particular procedure and sufficient to accommodate the tools and instrumentation needed for the procedure. Next a soft bladder in a deflated state is introduced into the abdominal cavity through the first incision. The neck of the balloon forms a gas-tight sealing contact (using a gasket) with a connector to the gas source. Once inserted, the soft bladder is inflated using pressurizing gas, e.g., $CO_2$ or other inert or physiologically benign gas (i.e. $N_2O$) via a separate inlet in the gasket. The bladder is selected so that it in its enlarged and inflated state it displaces internal organs that may be obstructing view and access to the organ to be operated on. The surgical instrumentation is introduced into the abdominal through the second incision. The location of the second incision is selected to provide an unhindered access to the organ of interest, once the soft bladder has been inflated to more obstructing organs aside. The material properties of the bladder allows the instrument to puncture a hole without leakage of the pressurized gas inside the bladder. Additional inserts can be made to introduce other bladders that can be inflated to provide additional maneuverability to organs, an example being the rotation of the liver to expose difficult to reach postsuperior segments (i.e. liver segments I, VII, VIII, IVa).

One advantage of certain embodiments of the invention is that the soft bladder can be resistant to or self-healing after puncture. Certain elastomeric polymers, such as silicone rubbers and polyurethanes, are sufficiently elastic so as to form a liquid- and gas-tight seal around a puncturing object such as a needle. In other embodiments, fibers can be embedded in the elastomeric wall to prevent propagation of tears. In cases where a sharp object punctures the soft bladder, a soft seal forms spontaneously around the hole and this seal maintained the functionality of the soft bladder. The self-sealing capabilities of the bladder allow for instruments to puncture the bladder without leakage. In one or more embodiments, a tool can be introduced through an input port at whatever orifice the surgeon inserts the bladder and then is punctured through the other side of the soft bladder when it reaches its target organ.

The self-healing properties of a soft expandable bladder is shown in FIG. 6. The soft expandable bladder was made from a composite material: polyaramid fibers embedded in an elastomeric matrix. It operates, in part, by the folding and unfolding of a quasi-bellows arrangement of pleats. The material system was polyaramid fibers (KevlarTMPulp, FibreGlast Inc.; 15 wt %) with lengths >1.0 mm, and average diameters, d~100 μm, blended into an uncured silicone matrix (Ecoflex 0030™, Smooth-On Inc.; 85 wt %) and the polyaramid fiber is readily available in a size range that blended well (via mixing with an impeller blade for 15 minutes) with the uncured silicone. Cellulose can be used in alternative embodiments. After blending, the mixture was a paste, but one that could still pour into the molds. The mixture was cured (60° C. for 30 minutes), and then bonded the resulting bellows to an inextensible flat composed of the same material. These blended composites are resistance to puncture and demonstrate extensibility sufficient to achieve significant ranges of motion.

Figure 6A:
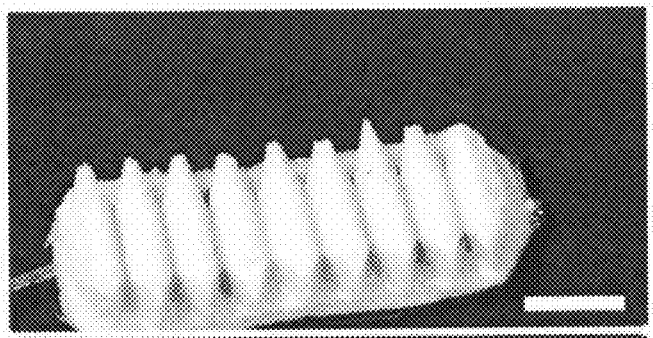
FIG. 6 is a series of photographs showing (a) a composite material, bellows-like soft body that (b) bends when pressurized. (c) The material seals around a puncture and the actuator continues to function, (d) even when the source of puncture (a 14 gauge needle) is removed. Scale bar is 2 cm.
Figure 6B:
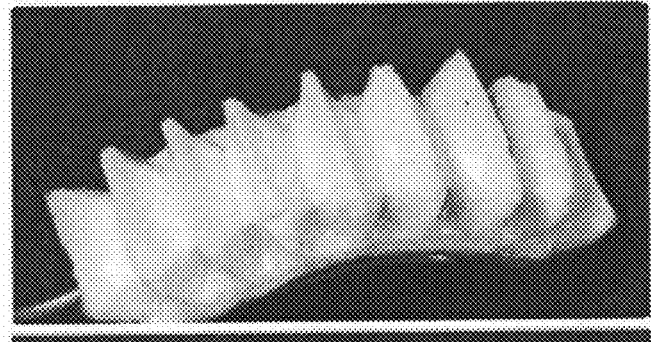
Figure 6C:
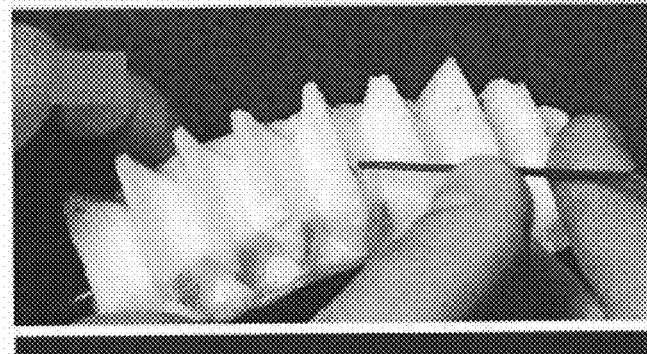
Figure 6D:

In cases where a sharp object punctured a soft body, a soft seal formed spontaneously around the hole and this seal maintained the functionality of the inflated soft bladder (FIG. 6A-6C). Even when the object was removed, the soft bladder continued to function (FIG. 6D). The fibers probably prevent crack propagation from expanding the damage due to the piercing object, and thus limit the extent of the crack to that of the piercing object itself. While not bound by any particular mode of operation, there are three primary mechanisms that may support the self-sealing phenomenon: (i) When a crack is created by an object, it pushes against and strains the bulk elastomer. Due to silicone's high resilience, when the object is removed the silicone returns to its original shape and presses the fresh crack surfaces against themselves—thus sealing the hole. (ii) The crack surfaces are deformable and conform to one another. The self-adhesion properties of PDMS (Sylgard 170; Dow Corning, Inc.) was measured and reported to have a work of adhesion, W, to be ~45 erg/cm2 (4.5 $\mu J/cm^2$) for that particular silicone elastomer. Using that value of W, an adhesive energy of ~9 erg (0.9 $\mu J$) is calculated for the hole created from the needle in FIG. 6C. (iii) While actuated, the internally pressurized bladder pushes the self-adhered crack inward and applies compressive force to seal the edges of the hole.

Although the present disclosure has been described and illustrated in the foregoing example embodiments, it is understood that the present disclosure has been made only by way of example, and that numerous changes in the details of implementation of the disclosure may be made without departing from the spirit and scope of the disclosure, which is limited only by the claims which follow. Other embodiments are within the following claims.

What is claimed is:

1. A surgical device for displacement of organs within a body cavity for providing at least visual access to a selected site, comprising:
    a molded, expandable bladder comprising a bellows-shaped first side and an inextensible flat second side, wherein the molded bladder defines a cavity having a selected geometry,
    wherein the bladder is configured to bend in a preferential direction when the bladder is inflated; and
    a valve in flow communication with the inflatable bladder for introduction of a pressurizing gas into the bladder.

2. The surgical device of claim 1, further comprising an insertion housing for housing the expandable bladder in an unexpanded state.

3. The surgical device of claim 1, wherein the bladder comprises fibers integrated into the bladder walls.

4. The surgical device of claim 1, further comprising at least one port in the expandable bladder adapted to allow a surgical instrument to pass therethrough.

5. The surgical device of claim 1, further comprising a laparoscopic tool including a flexible tube with a camera at its distal end.

6. The surgical device of claim 1, wherein the expandable bladder is self-sealing to punctures.

7. The surgical device of claim 1, wherein the bladder comprises polyaramid fibers embedded in an elastomeric matrix.

8. The surgical device of claim 1, wherein the valve is a one-way valve.

9. The surgical device of claim 1, wherein the valve is a two-way valve.

* * * * *